United States Patent [19]

Ravel

[11] 4,260,570
[45] Apr. 7, 1981

[54] METHOD AND APPARATUS FOR MAKING A VAGINAL CLEANING DEVICE

[75] Inventor: Kanak K. R. Ravel, Perth Amboy, N.J.

[73] Assignee: Block Drug Company Inc., Jersey City, N.J.

[21] Appl. No.: 38,139

[22] Filed: May 11, 1979

[51] Int. Cl.³ .............................................. B29C 23/00
[52] U.S. Cl. ................................... 264/46.6; 128/269
[58] Field of Search ............... 128/756, 759, 263, 267, 128/269, 285; 264/46.4, 46.9, 46.6; 425/444, 451.7, 469, 817 R; 521/63

[56] References Cited

U.S. PATENT DOCUMENTS

| | | | |
|---|---|---|---|
| 2,180,533 | 11/1939 | Leffler | 128/267 |
| 2,832,342 | 4/1958 | Wingenroth | 128/263 |
| 3,086,527 | 4/1963 | Forrest | 128/263 |
| 3,515,799 | 6/1970 | Ristuccia et al. | 264/46.9 |
| 3,674,025 | 7/1972 | Bleuer | 128/263 |
| 3,831,605 | 8/1974 | Fournier | 128/263 |
| 3,966,334 | 6/1976 | Forsberg | 128/269 |
| 3,985,951 | 10/1976 | Harris | 264/46.9 |
| 4,014,746 | 3/1977 | Greenspan | 128/269 |

Primary Examiner—robert W. Michell
Assistant Examiner—C. F. Rosenbaum
Attorney, Agent, or Firm—Ostrolenk, Faber, Gerb & Soffen

[57] ABSTRACT

A vaginal cleaning device is made by introducing foamable reactants into a container which is closed with a closure member having an elongated handle integral therewith and extending into the container. The reactants are permitted to form a cured foam in the container surrounding at least a portion of the handle extending into the container and the gas generated is vented through a vent opening in the closure member.

3 Claims, 4 Drawing Figures

METHOD AND APPARATUS FOR MAKING A VAGINAL CLEANING DEVICE

BACKGROUND OF THE INVENTION

Anatomically, the vagina is a tube, lined with mucus membrane. For all practical purposes, it is a cul-de-sac, open only at the external end because the cervical os is closed except during labor and is only open slightly during the menstrual flow and a few weeks postpartum. In the non-pregnant woman, the cervix will permit an instrument of very small caliber admission and even so, pressure is required to introduce it.

The normal vaginal secretions arise from Bartholin's glands, Skene's glands and the cervical glands. In the healthy, normal vagina, the secretions are clean, mucoid, and tenacious, and have high lubricating properties. In addition to the natural moistness of the vagina, there is always some debris present which consists of desquamating ephithilial cells. The debris may also include blood left from menstrual flow and the deposition of seminal fluid. Since the vaginal walls are normally approximated, most of the vaginal debris cannot be eliminated even by gravity.

Because body temperature is substantially constant, vaginal debris is largely protein material, and carbohydrate (as glycogen) is present, the vagina is an excellent incubator for a long list of pathogenic and non-pathogenic bacteria. The normal acidity exerts an inhibiting effect on the propagation of most pathogens but does not destroy them. These pathogens are therefore always present, ready to form the nucleus of an extensive growth at the first favorable change. Accordingly, the vagina should be kept clean and its cleansing should be a regular part of personal hygiene.

Many vaginal swabs or cleansers have been proposed as exemplified, for example, by U.S. Pat. No. 3,228,398 and others. It is obviously desirable to have available a disposable vaginal cleaning device of polyurethane or the like material premoistened with an aqueous solution containing surfactant(s), fragrance(s), medication(s), deodorant(s), germicide(s), etc. for the expeditious cleaning of the vagina. However, the complex chemistry of polyurethane foam manufacture and the high cost of shaping and postimpregnating shaped foams with cleansing solutions and making them available and protective packaging has retarded progress in the availability of a reasonably priced, safe and effective, portable and disposable internal vaginal cleaning material. Accordingly, it is the object of this invention to make available an economic method and apparatus for making a safe and effective, portable and disposal internal vaginal cleaning device containing an impregnated or non-impregnated foam material. This and other objects will become apparent to those skilled in the art from the following detailed description taken together with the figures which illustrate the four steps of the invention and show the package of the present invention.

SUMMARY OF THE INVENTION

This invention relates to vaginal cleaning devices and more particularly to a package and method for preparing a vaginal cleaning device. The package system serves as its own mold in which suitable chemical reactants can be mixed with a cleaning solution as desired to generate a mass of moist foam while the container-package is being finally assembled. The user upon opening the package will have available a premoistened foam device for personal vaginal hygiene and after use, the device can be placed back into its original case for disposal, thereby avoiding unslightly exposure of the foam now coated with vaginal fluid and debris.

DESCRIPTION OF THE INVENTION

Figure 1:
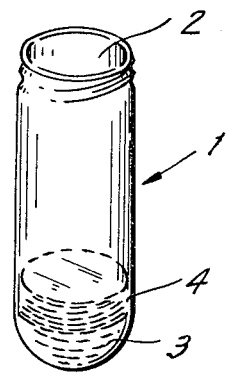
FIG. 1 is a perspective view of the container.

FIG. 1 shows a container 1 of the present invention which can be constructed from any suitable material which is inert to the foam reactants and foam and cleansing solution (if used). The interior of container 1 serves as a mold for formation of a polyurethane foam and is therefore appropriately shaped to the desired foam configuration. Container 1 is provided with a closure opening 2.

In the first step of the method of this invention, suitable foam reactants 3 and, if desired, a cleansing solution 4 are introduced into container 1. The reactants 3 are preferably for a hydrophilic polyurethane foam although other foamable reaction systems can be employed if desired. Various hydrophilic polyurethane and other foam systems are commercially available, one example of which being that sold under the trademark HYPOL by W. R. Grace & Co. Cleansing solution 4 is usually an aqueous solution containing surfactant(s), fragnance(s), medication(s), deodorant(s), germicide(s), etc. and various combinations thereof which have been heretofore used in vaginal cleaning devices.

Figure 2:
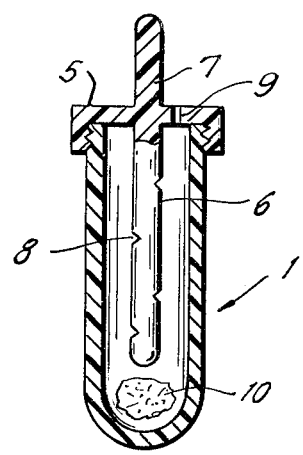
FIG. 2 is a view, partially in cross-section, of the container and closure member.

The balance of the apparatus of this invention and the second step in the method are shown in FIG. 2. As is apparent from the figure, closure opening 2 of container 1 is closed with a closure member 5 by any desired method such as by a pressure fit or by a screwtype operation. Closure member 5 includes an extension 6 adapted to extend into container 1. Extension 6 preferably is integral to, substantially perpendicular to, and extends beyond closure member 5 away from container 1 so as to provide a gripping member 7. If desired, extension 6 can be provided with notches or undulations 8 to facilitate a stronger bond with the foam to be produced. Closure member 5 is also provided with a vent opening 9. Closure member 5 and extension 6 can be constructed of any material which is inert to the foam reactants and cleansing solution. As is apparent from FIG. 2, the foamable reactants 3 usually begin to generate a mass of moist foam 10 incorporating cleansing solution 4 as closure member 5 is placed into position on closure opening 2 of container 1.

Figure 3:
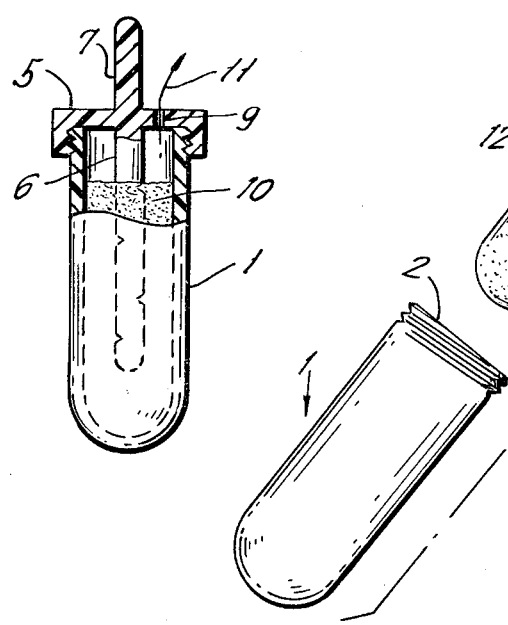
FIG. 3 is another view, partially in cross-section, of the container and closure member with foam formed.
Figure 4:
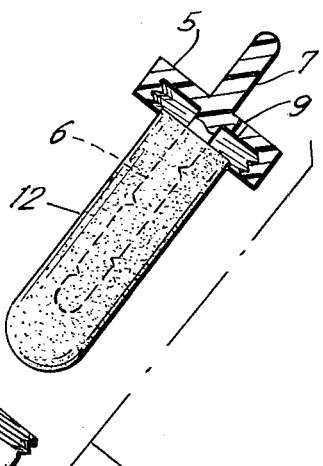
FIG. 4 is an exploded view, partially in cross-section, of the container separated from the closure member which carries the foam.

The foaming reaction is permitted to proceed (FIG. 3) until complete and the foam has cured. During this time, gases generated by the reaction are permitted to escape through vent opening 9 as indicated by arrow 11. Thereafter (FIG. 4) closure member 5 can be removed from container 1 in order to realize a disposal container (i.e. container 1) and a disposable vaginal cleansing device composed of closure member 5 with its gripping portion 7 and elongated extension 6, a portion of extension 6 carrying a mass of moist foam 12.

The present invention provides numerous advantages since both the product and the package are prepared simultaneously thereby realizing a savings in time, labor, equipment and materials of construction. The production technology is simplified compared to that used heretofore and the used product can be disposed of in a sanitary fashion.

It will be appreciated that various changes and modifications can be made in the process and apparatus of this invention without departing from the spirit and scope thereof. For example, vent opening 9 can be sealed by the use of a suitable cement or sealant after the foaming reaction is complete to prevent dehydration or drying of the moist foam during transit or storage of the device. The various embodiments which have been described hereinabove were for the purpose of further illustrating the invention but were not intended to limit it.

We claim:

1. A method of forming a vaginal cleansing device which comprises (1) introducing foamable reactants into a container inert thereto and having a closure opening adapted to be closed by a closure member; (2) closing said closure opening with a closure member having an elongated extension extending into said container and also having means to vent gas from said container; (3) forming a cured foam from said reactants in said container surrounding at least a portion of said extension extending into said container; and (4) separating said closure member and extension having one end surrounded by a cured foam from said container.

2. The method of claim 1, wherein the foamable reactants are foamable hydrophilic polyurethane foam reactants.

3. The method of claim 1, wherein a solution containing at least one surfactant, fragrance, medication, deodorant or germicide is introduced into said container before said closure opening is closed with said closure member.

* * * * *